United States Patent
Brill et al.

(10) Patent No.: US 6,650,424 B2
(45) Date of Patent: Nov. 18, 2003

(54) METHOD AND SYSTEM FOR MEASURING IN PATTERNED STRUCTURES

(75) Inventors: Boaz Brill, Rishon Lezion (IL); Moshe Finarov, Rehovoth (IL)

(73) Assignee: Nova Measuring Instruments Ltd., Rehovot (IL)

(*) Notice: Subject to any disclaimer, the term of this patent is extended or adjusted under 35 U.S.C. 154(b) by 0 days.

(21) Appl. No.: 10/005,118

(22) Filed: Dec. 7, 2001

(65) Prior Publication Data

US 2002/0090744 A1 Jul. 11, 2002

(30) Foreign Application Priority Data

Dec. 7, 2000 (IL) .................................................. 140179

(51) Int. Cl.$^7$ ............................................. G01B 11/00
(52) U.S. Cl. ...................... 356/601; 356/625; 356/635; 250/559.19
(58) Field of Search ..................... 356/604, 614, 356/625, 630, 635, 388, 394, 496, 503; 250/559.19, 559.44, 310; 430/8, 70

(56) References Cited

U.S. PATENT DOCUMENTS

| 5,607,800 | A | * | 3/1997 | Ziger ........................... 356/445 |
| 5,739,909 | A | * | 4/1998 | Blayo et al. ................. 356/381 |
| 5,867,276 | A | * | 2/1999 | McNeil et al. ............... 356/445 |
| 6,317,211 | B1 | * | 11/2001 | Ausschnitt et al. ......... 356/401 |
| 6,388,253 | B1 | * | 5/2002 | Su .............................. 250/310 |
| 6,407,373 | B1 | | 6/2002 | Dotan |
| 6,423,977 | B1 | * | 7/2002 | Hayasaki et al. ...... 250/559.19 |
| 6,433,871 | B1 | * | 8/2002 | Lensing et al. ............. 356/381 |

OTHER PUBLICATIONS

U.S. patent application Ser. No. 09/610,889, Finarov, filed Jun. 6, 2000.
C.J. Raymond et al., "Metrology of Subwavelength Photoresist Gratings Using Optical Scatterometry", *Journal of Vacuum Science & Technology B*, Jul. 1, 1995, pp. 1484–1495, vol. 13, No. 4.
C.J. Raymond et al., "Multiparameter Grating Metrology Using Optical Scatterometry", *Journal of Vacuum Science & Technology B*, Mar. 1, 1997, pp. 361–368, vol. 15, No. 2.
P. Burggraaf, "Persuing Advanced Metrology Solutions", *Semiconductor International*, Apr. 1994, pp. 62–64, vol. 17, No. 4.

* cited by examiner

Primary Examiner—Frank G. Font
Assistant Examiner—Sang H. Nguyen
(74) Attorney, Agent, or Firm—Browdy and Neimark, P.L.L.C.

(57) ABSTRACT

A measurement method and system are presented for measuring parameters of a patterned structure. Scatterometry and SEM measurements are applied to the structure, measured data indicative of, respectively, the structure parameters and lateral pattern dimensions of the structure are generated. The entire measured data are analyzed so as to enable using measurement results of either one of the scatterometry and SEM measurements for optimizing the other measurement results.

24 Claims, 2 Drawing Sheets

METHOD AND SYSTEM FOR MEASURING IN PATTERNED STRUCTURES

FIELD OF THE INVENTION

The present invention is generally in the field of measurement techniques and relates to a method and system for measuring patterned structures such as semiconductor wafers, by utilizing scatterometry. The invention is particularly useful for controlling a photolithography process.

BACKGROUND OF THE INVENTION

Scatterometry based measurement techniques rely on measurement and interpretation of the characteristics of light diffracted from a regular array of lines (grating or pattern). Scatterometry provides the ability to accurately reconstruct the line profile, allowing the measurement of line width or lateral dimensions of the pattern (the so-called critical dimension (CD) of a patterned structure), height, profile wall angle and additional profile information. The analysis of diffraction measurements is usually carried out using exact models, such as RCWT, allowing for accurate reconstruction of the whole profile.

Critical dimensions can also be measured by a scanning electron microscope known as CD-SEM. The CD-SEM measurement technique is based on measuring the scattering efficiency of a focused electron beam, which is scanned over the sample area. CD-SEM thus provides an accurate top view image allowing for extracting different lateral dimensions, such as line width (CD).

Although both of the above indicated techniques are capable of measuring CD, measurements carried out by these techniques are completely different, and therefore usually lead to different measurement results. The differences between these two techniques generally consist of the following:

CD-SEM provides an image, while scatterometry does not CD-SEM measures separate lines, while scatterometry measures line arrays (gratings), affecting both the type of information, i.e., an average over the lines, and the required measurement site. CD-SEM provides only the top view of a pattern i.e., lateral information (CD), while scatterometry provides also the pattern height and profile information Additionally, the size and price of a scatterometry based measurement system and a CD-SEM are quite different.

SUMMARY OF THE INVENTION

There is a need in the art to improve the quality of measurements in patterned structures, such as semiconductor wafers by providing a novel measurement method and system.

The main idea of the present invention consists of combining the benefits of scatterometry and CD-SEM measurements by integrating a scatterometry measurement tool with a CD-SEM tool. While each of these tools has its relatively strong and weak sides (as compared to the other tool), the combined operation of these tools yields better results, both in terms of accuracy and in terms of additional profile information, than those that can be provided by using either one of these tools. Such a combination involves more than just putting the tools one beside the other but rather sharing information between the two tools thereby improving each one's measurements beyond its current capability. Thus, a real added value is formed by the combination.

The physical integration of the two tools in a common system provides additional benefits, such as saving costs (e.g., common wafer handling system), increased through, reduced down time of the system, etc.

The applicability of the combined CDSEM-Scatterometry system according to the invention is not limited to any specific application. Typical applications requiring line width and line profile information can be found mainly, but not only, in the semiconductor and flat panel display fabrication industry, including, for example, microlithography (CD, photoresist profile, etc.), and etch (STI poly-silicone etch, trenches, etc.). Additional applications that require the profiling of repeatable features, which are arranged in a two-dimensional army such as via-holes, can also be measured using scatterometry and can thus benefit from the combined measurement system.

In accordance with one aspect of the present invention, there is thus provided a method of measuring g parameters of a patterned structure, the method comprising the steps of:
  (i) applying scatterometry measurements to the structure and generating measured data indicative of the structure parameters;
  (ii) applying scanning electron microscopy (SEM) measurements to the structure and generating measured data indicative of lateral pattern dimensions of the structure;
  (iii) analyzing the entire measured data to use measurement results of either one of the scatterometry and SEM measurements for optimizing the other measurement results.

It should be understood that the measurement results are representative of real values of parameters extracted from the respective measured data.

According to another aspect of the invention, there is provided a measurement system for measuring parameters of a patterned structure, the system comprising:
  (a) a scatterometry measurement tool operable to apply measurement to the structure and generate measured data indicative of the structure parameters;
  (b) a scanning electron microscope (SEM) measurement tool operable to apply SEM measurements to the structure and generate measured data indicative of lateral pattern dimensions of the structure;
  (c) a control system for operating the measurement tools to apply respective measurements, and analyzing the measured data so as to use measurement results of either one of the scatterometry and SEM measurement tools for opimizing measurement results of the other tool.

It should be understood that the term "tool" (scatterometry tool or CD-SEM tool) signifies a set of constructional elements operating together to irradiate a sample with respective incident radiation, detect a radiation response of the sample and generate measured data indicative thereof. More specifically, the scatterometry measurement tool typically comprises a spectrophotometer, while the CD-SEM tool comprises an electron beam column and a detector, for example for detecting secondary electrons.

Generally, the construction and operation of each of these tools may be of any known kind. With respect to a scatterometry measurement tool, it is preferably constructed and operated as that disclosed in co-pending U.S. patent application Ser. No. 09/610,889, assigned to the assignee of the present application.

Thus, in the measurement system of the present invention, the scatterometry measurement tool and the SEM measurement tool are linked to each other for sharing measured data indicative of pattern-related information. This data sharing can be achieved in several ways:

According to one embodiment of the present invention, the two measurement tools are associated with the same database and the same control unit, such that data interpretation and reporting of measurement results are carried out by one controlling module, which has full control and full information over the two measurement tools.

According to another embodiment of the invention, the two measurement tools are associated with the same database, such that all information measured by either tool is stored within the same database, however, each tool is controlled by a separate control unit.

According to yet another embodiment of the invention, the two measurement tools are associated with separate databases and control units, respectively. In this case, however, the measurement tools can "request" information from one another through a communication channel for any specific need (specific wafer specific measurement site, type of sites, etc.).

Additionally, the two measurement tools may be integrated in the physical sense, such that handling a measured sample is commonly done and controlled through a unified control unit. Such physical integration can be achieved in several ways. For example, the scatterometry measurement tool is applicable to a sample external to the CD-SEM chamber. In other words, a measurement zone of the scatterometry tool is located externally to the measurement zone of the CD-SEM. Another option consists of locating the scatterometry tool eternal to the CD-SEM chamber and locating the sample to be measured by both tools within the CD-SEM chamber. In this case, the chamber is formed with an optical window enabling scatterometry measurements through the window. Yet another possibility is to locate the scatterometry measurement tool and a sample to be measured inside the CD-SEM chamber.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1A:
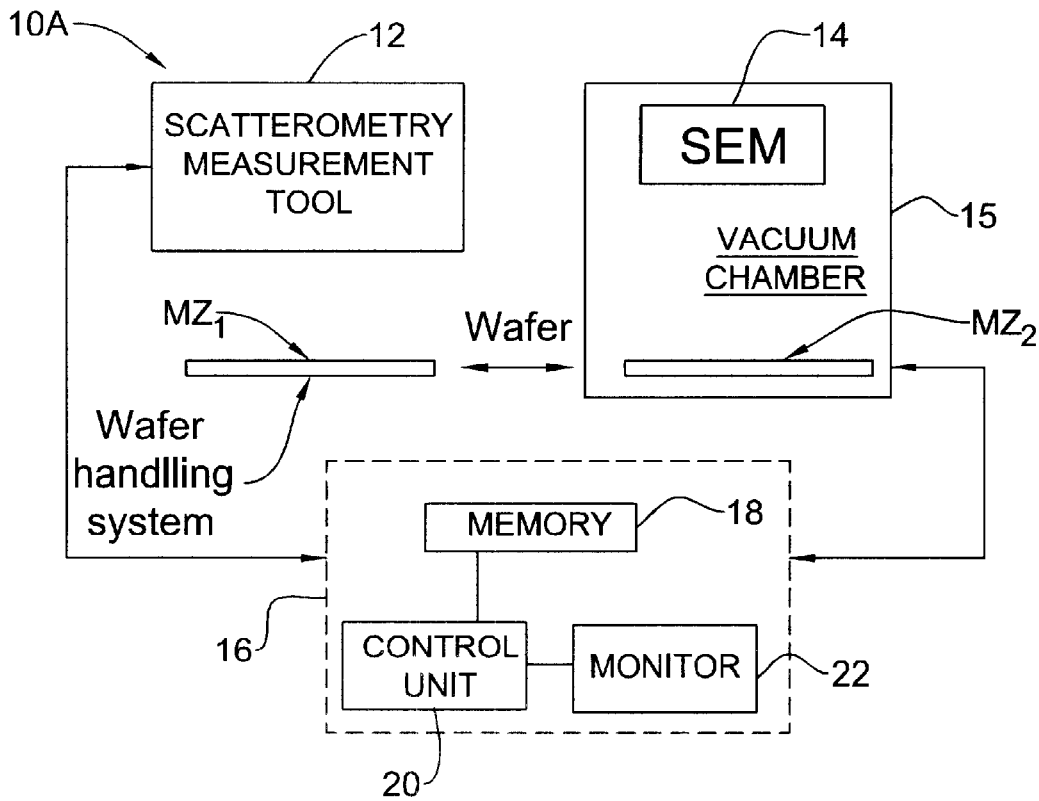
FIGS. 1A to 1C schematically illustrate three different examples, respectively, of a measurement system according to the invention.

Referring to FIG. 1A, there are illustrated by way of a block diagram the main components of a measurement system 10A according to one example of the invention. The system 10A comprises a scatterometry measurement tool 12 defining a first measurement zone $MZ_1$ where the scatterometry measurements are applied to a wafer (constituting a sample in the form of a patterned structure), a CD-SEM tool 14 defining a vacuum chamber 15 where a second measurement zone $MZ_1$ is located, in which CD-SEM measurements are applied to the wafer. In the present example, the first measurement zone is located outside the CD-SEM chamber. As further shown in the figure, output of the measurement tools 12 and 14 are connectable to a control system 16. The control system 16 is a computer system, preferably an expect system, including inter alia a memory unit 18 for storing a database representative of measured data, a control unit 20 (having data processing and analyzing utility), and a monitor 22 (constituting an output utility) for reporting the measurement results to the user.

Measurements are sequentially performed by the tools 12 and 14 (in either order), the wafer being transferred between the tools by a robot or any other conveying assembly (not shown). Generally wafer handling from one measurement tool to the other is possible. Thus, measured data produced by each measurement tool is stored in the common database (memory unit 18), and then analyzed by the same control unit 20, which also operates the measurement tools to actuate measurements. It should, however, be understood that the control system may include two separate control units for controlling the operation of the two measurement tools, respectively Alternatively, two separate databases may be used for storing measured data produced by the measurement tools, respectively.

Figure 1B:
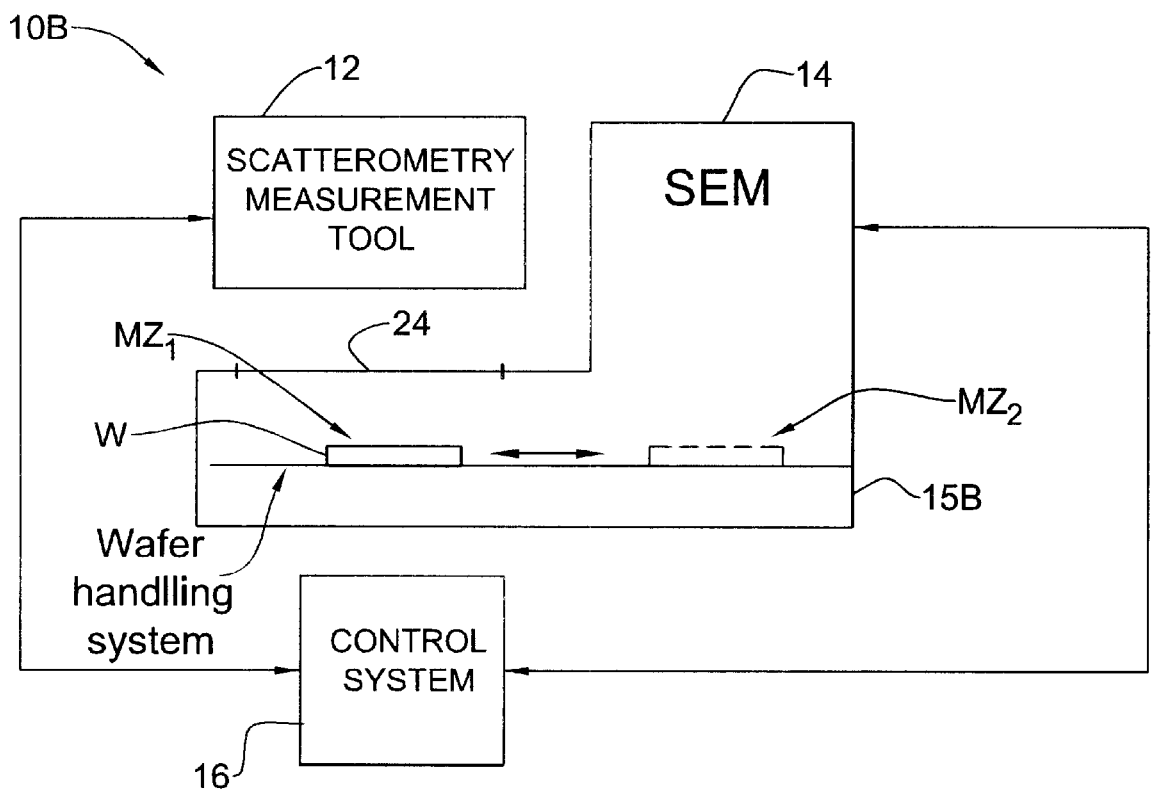
Figure 1C:
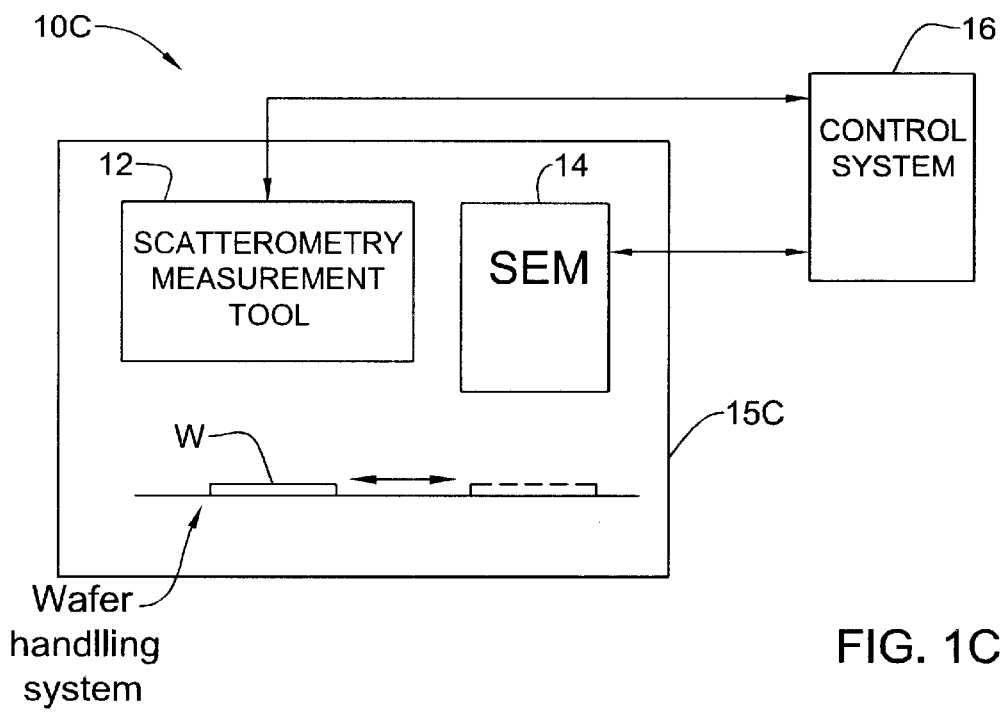

FIGS. 1B and 1C illustrate block diagrams of the man constructional parts of a measurement system according to two more examples, respectively, of the present invention. To facilitate understanding, the same reference numbers are used for identifying those components which are common in the examples of FIGS. 1A–1C.

Thus, a system 10B (FIG. 1B) comprises scatterometry and CD-SEM measurement tools 12 and 14, and a control system 16. Here, the first and second measurement zones $MZ_1$ and $MZ_2$ are located within the same area inside the CD-SEM chamber 15B. The chamber 15B is formed with an optical window 24 (i.e., a window transparent to radiation used for scatterometry measurement), and the measurement tool 12 is appropriately oriented with respect to the window 15B to enable measurements of the wafer W located inside the chamber within the measurement area. Appropriate translation means are provided for translating the wafer between the measurement zones $MZ_1$ and $MZ_2$. It should be understood, although not specifically shown that the control system 16 may be constructed and operated as described above, namely, may comprise the common database and common control unit for both measurement tools, the common database and separate control units, or the separate databases and separate control units.

In a measurements system 10C of FIG. 1C, the scatterometry measurement tool 12 is located inside the chamber 15C of the CD-SEM 14. In this case, the common measurement zone or separate measurement zones both located inside the chamber are used for locating the wafer therein during measurements. Similarly, either one of the above-described constructions of the control system 16 may be used. It should also be noted that location of the entire scatterometry measurement tool inside the vacuum chamber 15C is optional, and only an optical system or a part thereof may be located inside the chamber.

It should be understood that different line width (CD) measuring tools, e.g. CD-SEM, AFM, as well as different scatterometry techniques carry out measurements in a somewhat different manner, leading to significant offset between the measurement tools. These offsets are due mainly to the different ways in which different tools interact with the sample. Additionally, different calibration and interpretation algorithms used in different tools may also contribute to such offset. In fact, line width is frequently not well defined, since it varies as a function of features height (vertical dimension of the profile). It is thus difficult to calibrate between, tools that provide a unique number for line width (CD-SEM and tools that provide full profile information (scatterometry and AFM). Still for practical purposes, since the industry is currently used to rely on CD-SEM results, it is important to enable calibration of the scatterometry results to CD-SEM results. This enables the user to get the benefits of the complementing information the two tools provide without running into discrepancies causing the dilemma of deciding on which tool measurement results to rely. The problem is that these offsets are not constant, but rather depend on both the specific application and the type of profile. For example, CD-SEM measurement results are known to be dependent on the profile of the measured line (radius at top, slope at bottom, etc). No exact method for taking these dependencies into consideration exists, due to the complicated nature of the interaction between the electron beam and the sample. Thus, it is necessary to calibrate each type of profile separately, thereby complicating the calibration procedure.

Figure 2:
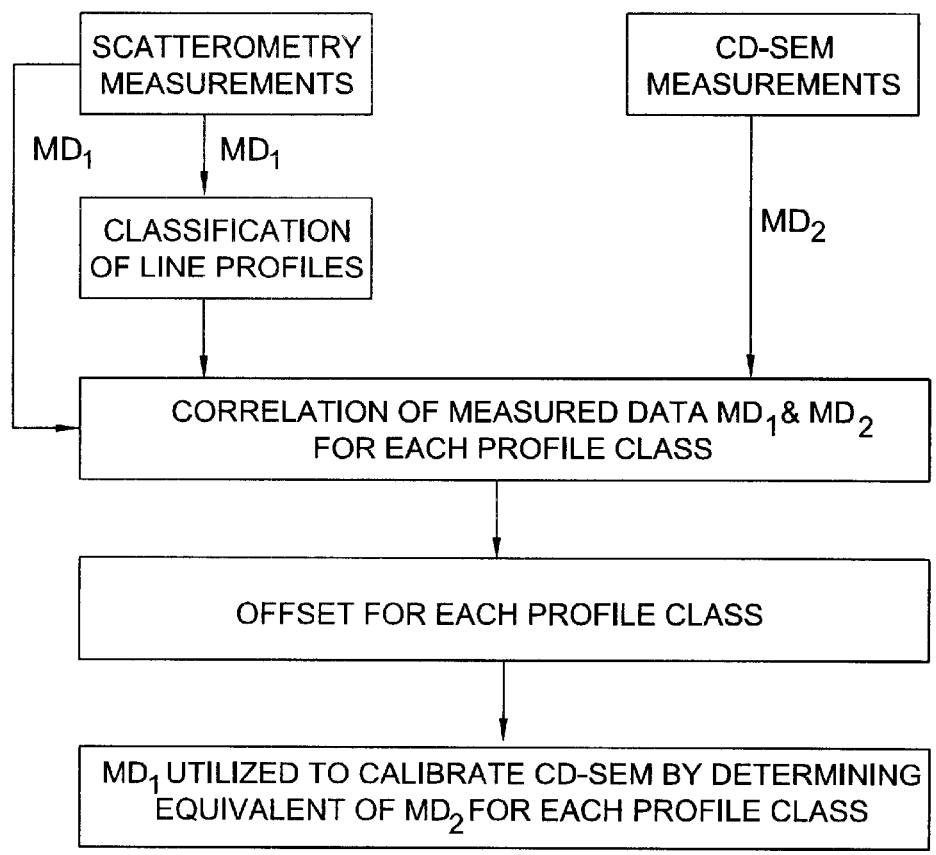
FIG. 2 is a flow chart of the main operation steps in calibrating the scatterometry and CD-SEM measurement tools of the system of either one of FIGS. 1A–1C.

The combined measurement system according to the invention (10A, 10B or 10C) provides an automatic way of calibrating both measurement tools to provide correlation between measurements results of these tools for every specific application, thereby providing the full benefits of the complementary information, without running into calibration problems. Using such a combined measurement system, it is possible to reach an accurate calibration between tools, in a manner described below with reference to FIG. 2.

A set of line arrays providing examples for different profile types (e.g. F-E matrix of a test structure) are measured using both the scatterometry and the CD-SEM tools, thereby providing measured data $MD_1$ and $MD_2$, respectively. The line profiles, as reconstructed by the scatterometry tools, are classified into several groups, e.g., according to wall slope at the bottom. Classification cam be done either using logical rules or using a learning system (neural network). CD results of both tools are correlated for each class of profiles separately, and the offset between the tools is established for each class. During a production run, once the profile is measured using scatterometry, the profile class is determined. Then, the offset value for the specific profile type can be used to accurately predict, based only upon scatterometry results, what is the equivalent CD-SEM result.

The present invention utilizing the combined measurements provides for improving scatterometry measurement results and the CD-SEM results in the system. The improvement of the scatterometry measurement results consists of the following.

In order to find the whole profile, scatterometry methods are required to fit many parameters that describe the profile geometry. The typical profile parameters that can be measured by the scatterometry measurement tool may include at least some of the following parameters:

line (feature) height (i.e. thickness);
total height of an envelope defined by the profile;
the height of the bottom-part trapezoid;
critical dimensions at the bottom and top of the feature region;
the average value of the critical dimension corresponding to the width of the envelope at a height equal to the half of the total height,
radius of the curvatures at the bottom and top of the feature region; and
the period of grating;
the tilt of the envelope with respect to the horizontal plane; and
the maximal distance between the profile and the envelope defined thereby.

Additionally, other parameters, such as heights of underling layers, may have to be fitted. Performing an optimization process in a multi-dimensional space is exponentially difficult with the number of dimensions. Typical problems may be long calculation time, results' stability, several local etc. By using CD-SEM results of the same or similar measurement sites in the wafer as initial conditions for the fitting process, the dimension of the problem may be somewhat reduced, improving fitting time and reducing the chance to "fall" into a local minimum. Although CD-SEM results cannot be taken "as is", it is possible to start from the CD-SEM results and limit the search within the database representative of the scatterometry measured data to a reasonable distance from the respective CD-SEM results. After all, after calibration between the tools, the results of the two measurement tools are not expected to be too far from each other. If it is still required to conserve the capability of the scatterometry to serve as an independent tool capable of detecting significant errors that may rarely happen to the CD-SEM, it is possible to define a more flexible fitting process. Such a two-step fitting process may be allowed to look for solutions that are far from those of the CD-SEM, only if a sufficiency good result is not found in the neighborhood of the CD-SEM result first.

The improvement of the CD-SEM results in the system consists of the following. As previously described, the most significant limitation of the CD-SEM is its inability to return profile information, although it is affected from the profile structure. This limitation way be somewhat overcome using the combined scatterometry-CDSEM system in one of several ways. The common idea is that although difficult to interpret, some profile information does exist in the CD-SEM signature (CDSEM signal across the line). This information is mostly lost when the signature is submitted to the threshold or other algorithm that extracts the CD result from the signature. A learning system (neural network) trained with both scatterometry profile results and CD-SEM signatures coming from the same sites, for the same application, could enable extraction of some profile information from the CD-SEM signatures. This could be done using one of the following methods: classification of profiles, profile extraction from CD-SEM sign, and re-normalization (gauging) of CD results, as described more specifically below.

Classification of Profiles

This method comprises the following operational steps:

Step 1: Profiles are classified into very broad types, such as "trapezoidal", "re-entrant" "rounded top", etc.

Step 2: Rules for mapping scatterometry profile results into these general types are defined.

Step 3: Scatterometry profile results and CD-SEM signatures are measured for a representative group of different profiles (e.g., on a Focus-Exposure matrix), such that both tools measure the same sites in the wafer.

Step 4: A neural net is trained to classify CD-SEM signatures according to the profile type, as found by the scatterometry. The input to the net is the CD-SEM signature, and the required output is the profile type.

During a production run, CD-SEM signatures are measured and submitted in parallel to the CD algorithm (as usual in CD-SEM) and to the classification neural network Both profile type (class) and the CD are reported to the user.

Profile Extraction from CD-SEM Signature

This technique is generally similar to the technique described above, but distinguishes therefrom in that one or more neural networks are trained to give specific profile parameters, as quantitative values, from the CD-SEM signature. For example, one net may be trained with the CD-SEM signature as input and the side wall angle as output. Another net may be trained to give top radius or another geometrical parameter of the patterned structure. Although such a measurement of profiles may be relatively inaccurate as compared to the simpler classification version, it may provide more information about the structure.

Re-Normalization (Gauging) of CD Results

Following the procedures described above, CD results of the CD-SEM may be improved in the sense that their dependence on the profile is reduced. As described above, it is expected that the offset between scatterometry and CD-SEM results depends on the profile type. This offset variation is, to a large extent, an artifact of the algorithm that is used for CD extraction from the CD-SEM signature. This artifact can be reduced in the following manner:

Calibration between scatterometry and CD-SEM results is carried out for every type of profile separately, and offset between scatterometry and CD-SEM is calculated for each profile type, as explained above.

A reference type of profile is chosen, e.g., trapezoidal,

The offset difference between different types and the reference type is calculated. For example, the difference between the offset (systematic difference between CD-SEM and scatterometry) measured for re-entrant profiles and the offset measured for trapezoidal profiles.

During a production run, once the CD and the type are identified, the CD result is corrected using the previously found difference.

Additionally, the technique of the present invention provides for correlating the die and scribe-line results. In this connection, it should be understood that one of the limitations of scatterometry is that it requires a measurement site with a periodic structure. Such structures are often impossible to find with the die, hence measurement has to be done in a special test site in the scribe line. The problem is that the correlation between scribe line measurements and in-die measurements is not clear, and some offset may exist between these two measurements due to effects such as loading effect.

By measuring sites both within the die and in the scatterometry test site, the CD-SEM can validate their correlation and find a possible offset. This information may be later utilized to calibrate scatterometry measurement carried out in the scribe line to the expected results (mainly CD) wink the die.

Another advantageous feature of the present invention is that it provides for using integrated scatterometry tools. Scatterometry is especially suited for integrated metrology. Thus, a Fab could include both a scatterometry-CDSEM system and integrated scatterometry tools. By building the scatterometry recipe on the scatterometry-CDSEM system, it is possible to calibrate the scatterometry results for the integrated tool, such that they fit to the CD-SEM results. If CD-SEM results are used as a baseline for the process (which is often the case), such calibration is of a very high value.

It should be understood that the technique of the present invention provides for controlling a manufacturing process applied to a patterned structure, for example photolithography. Indeed, by determining the parameters of a profile resulting from the manufacturing process, the working parameters of a processing tool can be adjusted to enable desired process results.

Those skilled in the art will readily appreciate that various modifications and changes can be applied to the embodiments of the invention as hereinbefore described without departing from its scope defined in and by the appended claims. In the method claims which follow, characters which are used to designate claim steps, are provided for convenience only and do not apply any particular order of performing the steps.

What is claimed is:

1. A method of measuring parameters of a patterned structure, the method comprising operating a handling system, operable for moving the patterned structure between first and second measurement zone, to locate the structure in a first measurement zone and support the structure during measurements, applying scatterometry measurements to the structure while in the first measurement zone, and generating first measured data presenting first measurement results indicative of at least one predetermined parameter of the structure;

operating sail handling system to locate the structure in a second measurement zone and support the structure during measurements, applying scanning electron microscopy (SEM) measurements to the structure in second measurement zone, and generating second measured data presenting second measurement results indicative of critical dimensions of the structure;

analyzing the first and second measured data to use either one of said first and second measurement results for optimizing the other measurement results.

2. The method according to claim 1, comprising calibrating between the first measured data and the second measured data, and generating calibration results, which are used for the optimization of at least one of said first and second measurement results.

3. The method according to claim 2, wherein said calibrating comprises:

applying both the scatterometry and the SEM measurements to a test structure, which is similar to said structure under measurements and has a set of different pattern profiles, thereby producing the first and second measured data, respectively, for each of said pattern profiles;

analyzing the first measured data to reconstruct the profiles and classify said profiles according to at least one profile parameter;

correlating the second measurement results indicative of the critical dimensions of said test structure as obtained from the first and second measured data for each of the profile classes, and establishing an offset value between the first and second measurement results for each profile class of the test structure; and using the offset value for a specific profile class to correct, the SEM measurement result for said specific profile class identified by the scatterometry measurement.

4. The method according to claim 1, wherein the scatterometry measurement results are obtained by analyzing the scatterometry measured data using fitting between said second measured data and corresponding data obtained with a theoretical model of the scatterometry measurements, the optimization of the scatterometry measurement results comprising selection the critical dimensions' parameter as obtained with the SEM measurements to be used in the fitting procedure.

5. The method according to claim 1, wherein the optimization of the SEM measurement results comprises analyzing the SEM measured data to obtain data indicative of structure parameters other than the critical dimensions of the pattern.

6. The method according to claim 5, wherein said analyzing of the SEM measured data comprises using of a learning mode trained with both the scatterometry measurement results and the SEM measured data.

7. The method according to claim 6, wherein the learn mode training comprises:
applying both the scatterometry and the SEM measurements to a test structure, which is similar to said structure under measurements and has a set of different pattern profiles, thereby producing the first and second measured data, respectively;
analyzing the first measured data to classify the profile patterns of the test structure into several groups, to thereby provide a map of the scatterometry profile results per said groups of the pattern profiles,
carrying out said learn mode training of an expert system to be responsive to the second measured data to determine the corresponding group of the profile patterns.

8. The method according to claim 7, wherein said profile patterns are classified in accordance with different shapes of the profile.

9. The method according to claim 8, wherein the profile shape includes at least one of the following: trapezoidal, re-entrant, rounded-top shapes.

10. The method according to claim 6, wherein the learn mode training comprises:
applying both the scatterometry and the SEM measurements to a test structure, having similar layers as in said structure under measurements and a set of different pattern profiles, thereby producing the first and second measured data, respectively;
analyzing the first measured data to determine values of the profile parameters,
carrying out said learn mode training of at least one expert system to be responsive to the second measured data to determine the corresponding values of the profile parameters.

11. The method according to claim 6, wherein the learn mode training comprises:
applying both the scatterometry and the SEM measurements to a test structure, having similar layers as in said structure under measurements and a set of different pattern profiles, thereby producing the first and second measured data, respectively;
analyzing the first measured data to classify the profile patterns into several groups, to thereby provide a map of the scatterometry profile results per said groups of the pattern profiles,
analyzing the second data so as to determine an offset between the first and second measured data for each of said groups;
carrying out said learn mode training of an expert system to be responsive to data indicative of an offset between the first and second measured data to determine the corresponding group of the profile patterns.

12. The method according to claim 1, for measuring in a semiconductor wafer, and also comprising correlating the measurement results obtained by measuring in a die and a scribe-line of a wafer, wherein measurements in the die include the SEM measurements, while the measurements in the scribe line includes the scatterometry and the SEM measurements.

13. The method according to claim 1, wherein the scatterometry measurements are applied to the structure while progressing on a production line, thereby enabling integrated process control.

14. A measurement system for measuring parameters of a patterned structure, the system comprising:
(a) a scatterometry measurement tool operable to apply measurements to the structure when located in a first measurement zone, and generate first measured data presenting first measurement results indicative of at least one predetermined parameter of the structure characterizing a file of the pattern;
(b) a scanning electron microscope (SEM) measurement tool operable to apply SEM measurements to the structure when located in a second measurement zone, and generate second measured data presenting second measurement results indicative of critical dimensions of the patterned structure;
(c) a handling system operable for moving the structure between the first and second measurement zones and supporting the structure during measurements;
(d) a control system for selectively operating the scatterometry measurement tools and the SEM measurement tool to apply respective measurements to the structure, the control system having a data processing and analyzing utility preprogrammed to be responsive to the first and second measured data and analyzing said data by using either one of first and second measurement results for optimizing the other of the first and second measurement results of the other tool.

15. The system according to claim 14, wherein said SEM measurement tool has a vacuum chamber, in which the structure under measurements is located, said scatterometry measurement tool being located outside said chamber for applying scatterometry measurements to the structure through an optical window made in the chamber.

16. The system according to claim 14, wherein at least an optical arrangement of the scatterometry measurement tool for directing radiation to and from the structure is located inside a vacuum chamber of the SEM measurement tool.

17. A method of measuring parameters of a patterned structure, the method comprising:
(a) applying scatterometry measurements to the structure while located in a first measurement zone, and generating first measured data presenting first measurement results indicative of at least one predetermined parameter of the structure;
(b) applying scanning electron microscopy (SEM) measurements to the structure while located in a second measurement zone, and generating second measured data presenting second measurement results indicative of critical dimensions of the structure;
(c) analyzing the first and second measured data to use said first measurement results for optimizing the q second measurement results.

18. The method according to claim 17, wherein the analyzing of the SEM measured data comprises using a learning mode trained with both the scatterometry and SEM measured data.

19. The method according to claim 18, wherein the learn mode training comprises:
applying both the scatterometry and the SEM measurements to a test structure, which is similar to said structure under measurements and has a set of different pattern profiles, thereby producing the first and second measured data, respectively;
analyzing the first measured data to classify the profile patterns of the test structure into several groups, to thereby provide a map of the scatterometry profile results per said groups of the pattern profiles,
carrying out said learning mode training of an expert system to be responsive to the second measured data to determine the corresponding group of the profile patterns.

20. The method according to claim 19, wherein said profile patterns are classified in accordance with different shapes of the profile.

21. The method according to claim 20, wherein the profile shape includes at least one of the following: trapezoidal, re-entrant, rounded-top shapes.

22. The method according to claim 18, wherein the learn mode training comprises:

applying both the scatterometry and the SEM measurements to a test structure, having similar layers as in said structure under measurements and a set of different pattern profiles, thereby producing the first and second measured data, respectively;

analyzing the first measured data to determine values of the profile parameters, carrying out said learn mode training of at least one expert system to be responsive to the second measured data to determine the corresponding values of the profile parameters.

23. The method according to claim 18, wherein the learn mode training comprises:

applying both the scatterometry and the SEM measurements to a test structure, having similar layers as in said structure under measurements and a set of different pattern profiles, thereby producing the first and second measured data, respectively;

analyzing the first measured data to classify the profile patterns into several groups, to thereby provide a map of the scatterometry profile results per said groups of the pattern profiles, analyzing the second data so as to determine an offset between the first and second measured data for each of said groups;

carrying out said learn mode training of an expert system to be responsive to data indicative of an offset between the first and second measured data to determine the corresponding group of the profile patterns.

24. A method of measuring parameters of a patterned structure, the method comprising:

(a) applying scatterometry measurements to the structure while located in a first measurement zone, and generating first measured data presenting first measurement results indicative of at least one predetermined parameter of the structure;

(b) applying scanning electron microscopy (SEM) measurements to the structure while located in a second measurement zone, and generating second measured data presenting second measurement results indicative of critical dimensions of the structure;

(c) analyzing the first and second measured data to use said first measurement results for optimizing the second measurement results to include data indicative of structure parameters other than the critical dimensions of the pattern.

* * * * *

UNITED STATES PATENT AND TRADEMARK OFFICE
CERTIFICATE OF CORRECTION

PATENT NO.    : 6,650,424 B2
DATED         : November 18, 2003
INVENTOR(S)   : Brill et al.

It is certified that error appears in the above-identified patent and that said Letters Patent is hereby corrected as shown below:

Column 8,
Line 19, after "structure" insert -- while--;

Column 9,
Line 58, delete "includes" and insert therefor -- include --;

Column 10,
Line 4, delete "file" and insert therefor -- profile --;
Line 15, delete "tools" and insert therefor -- tool --;
Line 46, after "the: delete "q".

Signed and Sealed this

Fifteenth Day of June, 2004

JON W. DUDAS
*Acting Director of the United States Patent and Trademark Office*